US008249324B2

United States Patent
Yokota et al.

(10) Patent No.: US 8,249,324 B2
(45) Date of Patent: Aug. 21, 2012

(54) IMAGE PROCESSING APPARATUS, IMAGE PROCESSING PROGRAM, STORAGE MEDIUM, AND ULTRA-SONIC DIAGNOSTIC APPARATUS

(75) Inventors: Yasunari Yokota, Gifu (JP); Rie Taniguchi, Gifu (JP); Yoko Kawamura, Gifu (JP); Fumio Nogata, Gifu (JP)

(73) Assignee: Gifu University (JP)

( * ) Notice: Subject to any disclaimer, the term of this patent is extended or adjusted under 35 U.S.C. 154(b) by 133 days.

(21) Appl. No.: 12/808,620

(22) PCT Filed: Mar. 24, 2008

(86) PCT No.: PCT/JP2008/055360
§ 371 (c)(1),
(2), (4) Date: Jun. 16, 2010

(87) PCT Pub. No.: WO2009/081598
PCT Pub. Date: Jul. 2, 2009

(65) Prior Publication Data
US 2011/0105901 A1    May 5, 2011

(30) Foreign Application Priority Data

Dec. 20, 2007  (JP) ................................. 2007-328326

(51) Int. Cl.
*G06K 9/00* (2006.01)
(52) U.S. Cl. ......... 382/128; 382/131; 382/132; 600/437
(58) Field of Classification Search .......... 600/437–466; 382/128–132
See application file for complete search history.

(56) References Cited

U.S. PATENT DOCUMENTS

| 6,176,832 | B1 | 1/2001 | Habu et al. | |
| 6,554,774 | B1 * | 4/2003 | Miele | 600/485 |
| 7,048,691 | B2 * | 5/2006 | Miele et al. | 600/504 |
| 7,503,896 | B2 * | 3/2009 | Miele et al. | 600/454 |

(Continued)

FOREIGN PATENT DOCUMENTS

JP    11-076233 A    3/1999

(Continued)

OTHER PUBLICATIONS

Nakagawa, et al., "Imaging of Cross-Sectional Elasticity in Short-Axis Plane of Arterial Wall by Transcutaneous Ultrasound," 2003 IEEE Ultrasonics Symposium, pp. 1887-1890.

(Continued)

*Primary Examiner* — Sanjay Cattungal
(74) *Attorney, Agent, or Firm* — Caesar, Rivise, Bernstein, Cohen & Pokotilow, Ltd.

(57) ABSTRACT

A computer 12 of an image processing apparatus 11 acquires a moving image including a minor axis cross section of a carotid artery and a cross section of surrounding tissues around the carotid artery and estimates, from images of two temporally different frames of the acquired moving image, an optical flow of each point included in an area corresponding to a carotid artery wall and an optical flow of each point included in an area corresponding to the surrounding tissues. Based on the estimated optical flow of each point, the computer 12 calculates an amount of displacement of the carotid artery and the surrounding tissues with respect to a radial direction of the carotid artery depending on a change in internal pressure of the carotid artery. The computer 12 also calculates an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder. The computer 12 calculates the elastic modulus of the carotid artery wall and the elastic modulus of the surrounding tissues so as to minimize a square error between the two calculated amounts of displacement.

5 Claims, 5 Drawing Sheets

U.S. PATENT DOCUMENTS

| | | | |
|---|---|---|---|
| 2002/0055680 A1* | 5/2002 | Miele et al. ............... | 600/450 |
| 2002/0062086 A1* | 5/2002 | Miele et al. ............... | 600/483 |
| 2005/0038346 A1* | 2/2005 | Miele ........................ | 600/485 |
| 2006/0206032 A1* | 9/2006 | Miele et al. ............... | 600/504 |
| 2009/0012399 A1* | 1/2009 | Sunagawa et al. ........ | 600/454 |

FOREIGN PATENT DOCUMENTS

| | | |
|---|---|---|
| JP | 2002-209857 A | 7/2002 |
| JP | 2006166955 | 6/2006 |
| JP | 2006-263128 A | 10/2006 |
| JP | 3882084 B2 | 11/2006 |
| JP | 20070268303 | 10/2007 |

OTHER PUBLICATIONS

Supplementary European Search Report dated Mar. 30, 2011 re Application No. EP 08 72 2676.

International Search Report for PCT/JP2008/055360.

K. Hayashi, et al., "Parametric Description . . . :", Journal of Japanese Society of Biorheology, vol. 3, pp. 75-78 (1980).

T. Kawasaki, et al., "Non-Invasive . . . ", Cardiovascular Research, 21, 9 (1987), pp. 678-687.

International Preliminary Report on Patentability for PCT/JP2008/055360 issued Jul. 20, 2010.

* cited by examiner

$r_1$: INNER RADIUS (mm)
$r_2$: OUTER RADIUS (mm)
P: INTERNAL PRESSURE (kPa)
$E_1$, $E_2$: ELASTIC MODULUS (kPa)
$v_1 = v_2 = 0.5$: POISSON'S RATIO

IMAGE PROCESSING APPARATUS, IMAGE PROCESSING PROGRAM, STORAGE MEDIUM, AND ULTRA-SONIC DIAGNOSTIC APPARATUS

TECHNICAL FIELD

The present invention relates to an image processing apparatus, an image processing program, a storage medium, and ultrasonic diagnostic equipment, and particularly, to an image processing apparatus and an image processing program for an ultrasound image of a carotid artery as well as a storage medium and ultrasonic diagnostic equipment related to the image processing apparatus and the image processing program.

BACKGROUND OF THE INVENTION

Arteriosclerosis is one of the lifestyle-related diseases in which excessive lifestyle habits are risk factors. Arteriosclerosis advances from youth with very few symptoms, and if left untreated, arteriosclerosis may develop into cerebral infarction, cardiac infarction, angina pectoris, and the like. It is difficult to cure arteriosclerosis. Therefore, it is important to find symptoms of arteriosclerosis at an early stage and prompt the patients to improve lifestyle habits to slow down the progression of the diseases.

There are various diagnostic methods for examining arteriosclerosis. Among the methods, ultrasonic echo examination allows noninvasive direct observation of blood vessels and is an indispensable examination in the current clinical diagnosis. The carotid artery ultrasonic echo examination for arteriosclerosis diagnosis evaluates the presence of plaque and intima-media complex thickness (IMT). However, at an early stage of arteriosclerosis, there is no plaque, and the IMT is thin. It is difficult to find symptoms at an early stage of arteriosclerosis in the morphological observation by ultrasonic echo examination.

As contrasted with this, since arteriosclerosis is sclerosis of artery and loss of elasticity, there is an idea that movements of artery associated with heartbeats can be evaluated. Various indicators of the degree of arteriosclerosis based on evaluations related to the excellence of behaviors of artery have been proposed.

For example, Non-Patent Documents 1 and 2 propose stiffness parameters and modified stiffness parameters, respectively.

$$\beta^* = \frac{\ln P_s - \ln P_d}{\left(\frac{D_s - D_d}{D_d}\right)} \quad (1)$$

The above Equation (1) shows a calculation of the modified stiffness parameter. In Equation (1), $P_s$ denotes blood pressure systolic of a carotid artery, $P_d$ denotes blood pressure diastolic of the carotid artery, $D_s$ denotes maximum diameter of the carotid artery at blood pressure systolic, and $D_d$ denotes minimum diameter of the carotid artery at blood pressure diastolic. In Equation (1), the difference between the blood pressure systolic and blood pressure diastolic of the carotid artery is normalized by the excellence of behavior of the carotid artery. The Equation (1) indicates that the greater the value of $\beta^*$ is, the worse the behavior of carotid artery becomes considering the blood pressure difference, or the stiffer the carotid artery is.

In Patent Document 1, the carotid artery is assumed to be a thick cylinder with a thickness d, and an elastic modulus $E_{th}$ of the carotid artery is calculated according to the following Equation (2) based on the mechanical characteristics of distortion and stress. In Equation (2), d denotes the thickness of a blood vessel wall.

$$E_{th} = \frac{P_s - P_d D_d (D_d + 2d)}{\frac{D_s - D_d}{D_d} 2d(D_d + d)} \quad (2)$$

Surrounding tissues, such as fat, existing around the carotid artery are not taken into consideration in all the documents described above. However, the behavior of a carotid artery is influenced by the surrounding tissues in no small part. The conventional methods cannot distinguish whether the restricted movement of a carotid artery is caused by sclerosis of the carotid artery or by stiffness of the surrounding tissues of the carotid artery.

Patent Document 1: Japanese Patent No. 3882084

Non-Patent Document 1: Hayashi K, Nakagawa S, Naruto Y, Moritake K, Okumura A, "Parametric description of mechanical behavior of arterial walls", Journal of Japanese Society of Biorheology, 3 (1980), pp. 75-78.

Non-Patent Document 2: Kawasaki T, Sasayama S, Yagi S, Asakawa T, Hirai T, "Non-invasive assessment of the age related changes in stiffness of major branches of the human arteries", Cardiovasc Res, 21, 9 (1987), pp. 678-687.

SUMMARY OF THE INVENTION

Accordingly, an objective of the present invention is to provide an image processing apparatus and an image processing program capable of more accurately calculating an elastic modulus of a carotid artery wall by taking surrounding tissues of the carotid artery into consideration.

Another objective of the present invention is to provide a storage medium storing the image processing program and ultrasonic diagnostic equipment connected to the image processing apparatus for use.

To achieve the foregoing objectives, a first aspect of the present invention provides an image processing apparatus comprising: first calculation means for acquiring a moving image including a minor axis cross section of a carotid artery and a cross section of surrounding tissues around the carotid artery, estimating, from images of two temporally different frames of the acquired moving image, an optical flow of each point included in an area corresponding to a carotid artery wall and an optical flow of each point included in an area corresponding to the surrounding tissues, and calculating, based on the estimated optical flow of each point, an amount of displacement of the carotid artery and the surrounding tissues with respect to a radial direction of the carotid artery depending on a change in internal pressure of the carotid artery; and second calculation means for calculating an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder and calculating the elastic modulus of the carotid artery wall and the elastic modulus of the surrounding tissues so as to minimize a square error between the thus calculated amount of displacement and the amount of displacement calculated by the first calculation means.

Preferably, the first calculation means estimates the optical flow of each point on an axis extending in the radial direction of the carotid artery from the images of the two frames and calculates, based on the estimated optical flow of each point, the amount of displacement of the carotid artery and the surrounding tissues with respect to the radial direction of the carotid artery depending on a change in the internal pressure of the carotid artery.

A second aspect of the present invention provides an image processing program causing a computer to function as: first calculation means for acquiring a moving image including a minor axis cross section of a carotid artery and a cross section of surrounding tissues around the carotid artery, estimating, from images of two temporally different frames of the acquired moving image, an optical flow of each point included in an area corresponding to a carotid artery wall and an optical flow of each point included in an area corresponding to the surrounding tissues, and calculating, based on the estimated optical flow of each point, an amount of displacement of the carotid artery and the surrounding tissues with respect to a radial direction of the carotid artery depending on a change in internal pressure of the carotid artery; and second calculation means for calculating an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder and calculating the elastic modulus of the carotid artery wall and the elastic modulus of the surrounding tissues so as to minimize a square error between the thus calculated amount of displacement and the amount of displacement calculated by the first calculation means.

Preferably, the first calculation means estimates the optical flow of each point on an axis extending in the radial direction of the carotid artery from the images of the two frames and calculates, based on the estimated optical flow of each point, the amount of displacement of the carotid artery and the surrounding tissues with respect to the radial direction of the carotid artery depending on a change in the internal pressure of the carotid artery.

A third aspect of the present invention provides a storage medium storing the image processing program according to the second aspect.

A fourth aspect of the present invention provides ultrasonic diagnostic equipment connected to the image processing apparatus according to the first aspect. The ultrasonic diagnostic equipment generates an ultrasound B-mode image based on an echo signal obtained through transmission and reception of ultrasound by a probe and outputs the generated ultrasound B-mode image to the image processing apparatus.

BRIEF DESCRIPTION OF THE DRAWINGS

FIG. 7($a$) is a diagram showing an ultrasound B-mode image;

FIG. 7($b$) is a graph of the result of calculation according to an optical-flow technique, showing the amount of displacement of a carotid artery and the surrounding tissues with respect to the radial direction of the carotid artery at points on an axis extending in the radial direction of the carotid artery;

FIG. 8($a$) is a graph showing an amount of displacement h(r), which is least-squares-estimated according to a method of the present invention, together with an amount of displacement h(r) calculated according to the optical-flow technique;

FIG. 8($b$) is a graph showing an amount of displacement h(r), which is least-squares-estimated according to a conventional method, together with the amount of displacement h(r) calculated according to the optical-flow technique;

FIGS. 9($a$) and 9($b$) are graphs showing results when the same measurements are performed after changing the subject from the measurements the results of which are shown in FIGS. 8($a$) and 8($b$), FIGS. 9($a$) and 9($b$) corresponding to FIGS. 8($a$) and 8($b$), respectively; and FIGS. 10($a$) and 10($b$) are graphs showing results when the same measurements are performed after changing the subject from the measurements the results of which are shown in FIGS. 8($a$) and 8($b$) as well as in FIGS. 9($a$) and 9($b$), FIGS. 10($a$) and 10($b$) corresponding to FIGS. 8($a$) and 8($b$), respectively.

DETAILED DESCRIPTION OF THE PREFERRED EMBODIMENTS

Hereinafter, one embodiment of the present invention will be described with reference to FIGS. 1 to 10($b$).

Figure 1:
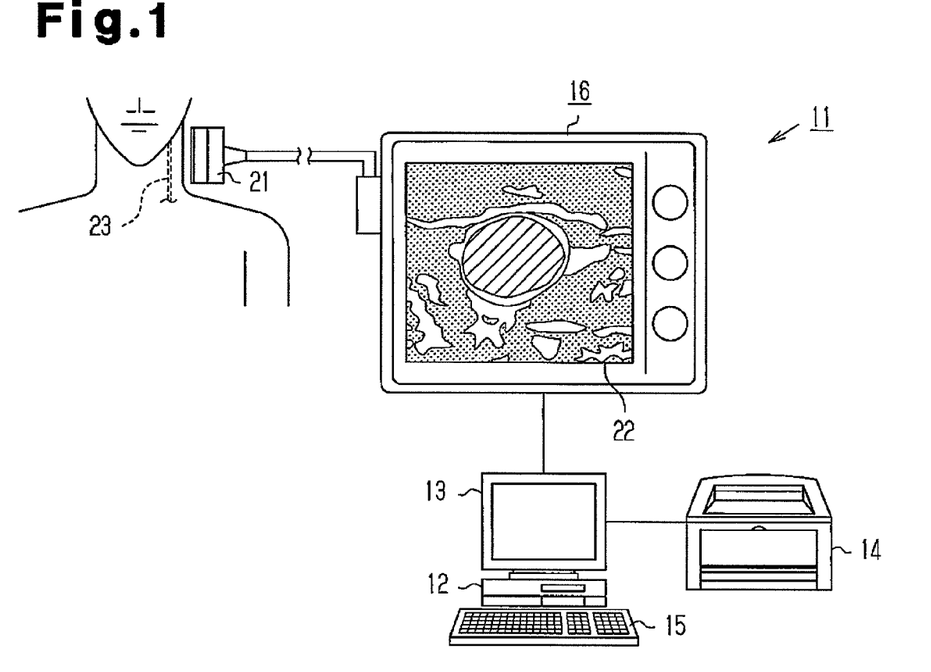
FIG. 1 is a schematic diagram of an image processing apparatus according to one embodiment of the present invention.

As shown in FIG. 1, an image processing apparatus 11 of the present embodiment comprises a computer 12 that functions as first calculation means (first calculation unit), second calculation means (second calculation unit), and storage means (storage unit), a display 13, a printer 14, a keyboard 15, and ultrasonic diagnostic equipment 16.

The ultrasonic diagnostic equipment 16 includes a probe 21, a display part 22, and an ultrasound source (not shown). The probe 21 of the ultrasonic diagnostic equipment 16 includes a tip end surface for transmitting a pulse wave in a living body and for receiving reflected waves (echo signal) from a carotid artery 23. The tip end surface of the probe 21 is formed in a rectangular shape. The ultrasonic diagnostic equipment 16 generates echo moving images (thus, a plurality of ultrasound B-mode images) that are acquired in a B-mode based on the echo signal and include minor axis cross sections of the carotid artery and cross sections of surrounding tissues around the carotid artery. The display part 22 of the ultrasonic diagnostic equipment 16 displays variations, such as expansion and contraction, of the carotid artery 23 of a subject in moving images.

The ultrasound B-mode images are outputted from a video output of the ultrasonic diagnostic equipment 16, video captured by a DV converter (not shown) at a predetermined resolution (m×n pixels) and predetermined frames per second, and then inputted to the computer 12 as an IEEE 1394 signal. Although 30 frames/second is selected as the predetermined frames per second in the present embodiment, the value is not limited to this. The value can be any value as long as it allows clear observation of variation in the carotid artery associated with heartbeats.

The number of pixels of an ultrasound image region displayed on the display 13 is represented by Nx in the horizontal direction and Ny in the vertical direction. In the present embodiment, although Nx=540 (pixels) and Ny=420 (pixels) are selected, the numbers are not limited.

The echo moving images acquired by the ultrasonic diagnostic equipment 16 are inputted to the computer 12, and then stored in a storage device 44 (see FIG. 2) incorporated in the computer 12. The storage device 44, which is made up of, for example, a hard disk or a semiconductor storage device, can read and write various information.

Figure 2:
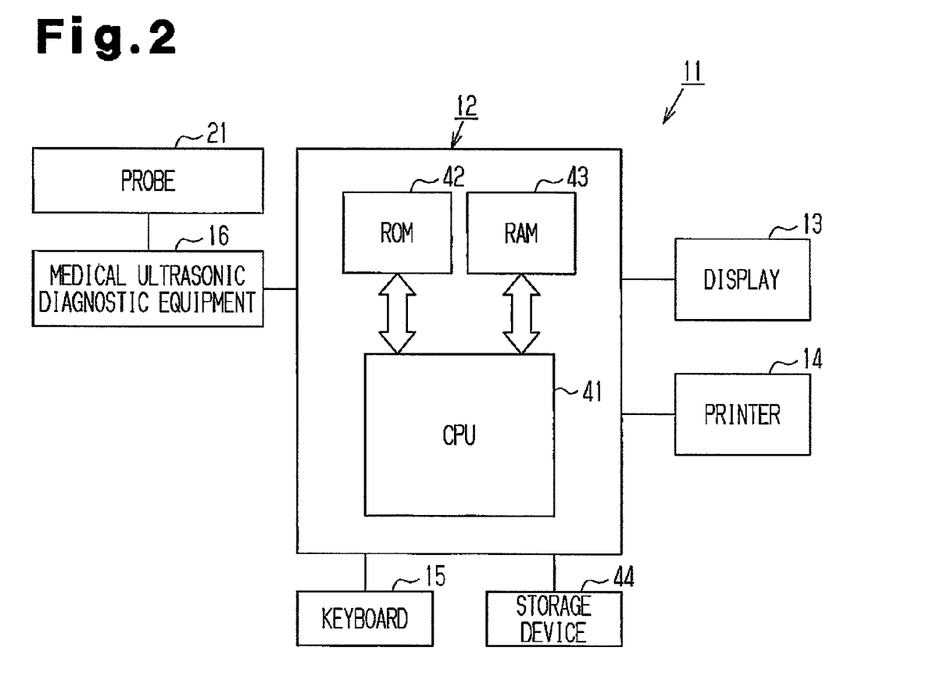
FIG. 2 is a schematic electrical block diagram of the image processing apparatus of FIG. 1.

As shown in FIG. 2, the computer 12 includes a central processing unit (CPU) 41, a ROM 42, and a RAM 43 and executes an image processing program stored in the ROM 42 as a storage medium. The RAM 43 is a working memory for executing the program.

Operation of Embodiment

Next, a process of the image processing program executed by the CPU 41 in the image processing apparatus 11 configured as described above will be described. Before the description of the program processing, "stress and distortion characteristics of carotid artery and surrounding tissues" and "two-layer cylindrical model" will be described.

(Stress and Distortion Characteristics of Carotid Artery and Surrounding Tissues)

Carotid arteries repeat expansion and contraction by heartbeats. Surrounding tissues, such as fat, around the carotid arteries expand and contract in association with the expansion and contraction of the carotid arteries. In general, the relationship between the stress and distortion of substance is examined from the perspective of strength of materials.

Figure 3:
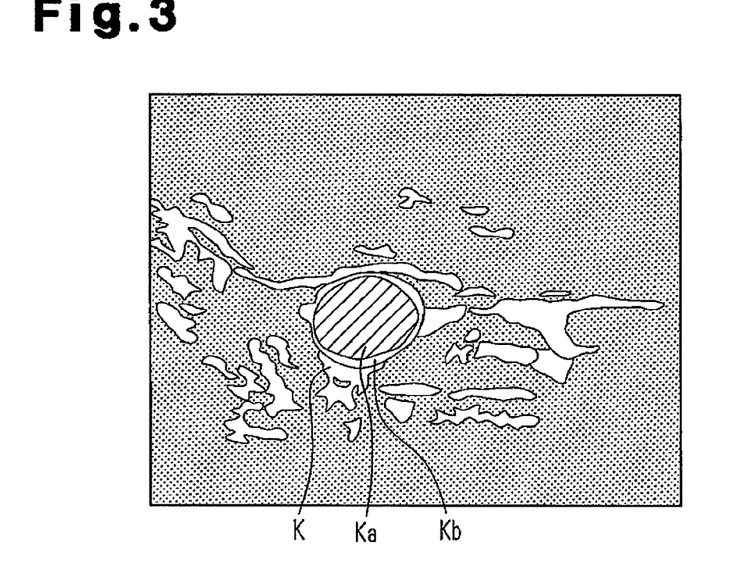
FIG. 3 is a diagram showing an ultrasound B-mode image.

FIG. 3 shows an ultrasound B-mode image including a minor axis cross section of carotid artery. A circular carotid artery K is shown at substantially the center in FIG. 3. In the ultrasound B-mode image, a carotid artery lumen Ka hatched in FIG. 3 is depicted in black, and a carotid artery wall Kb is depicted in white. The carotid artery is surrounded by surrounding tissues such as fat.

(Two-Layer Cylindrical Model)

Figure 4:
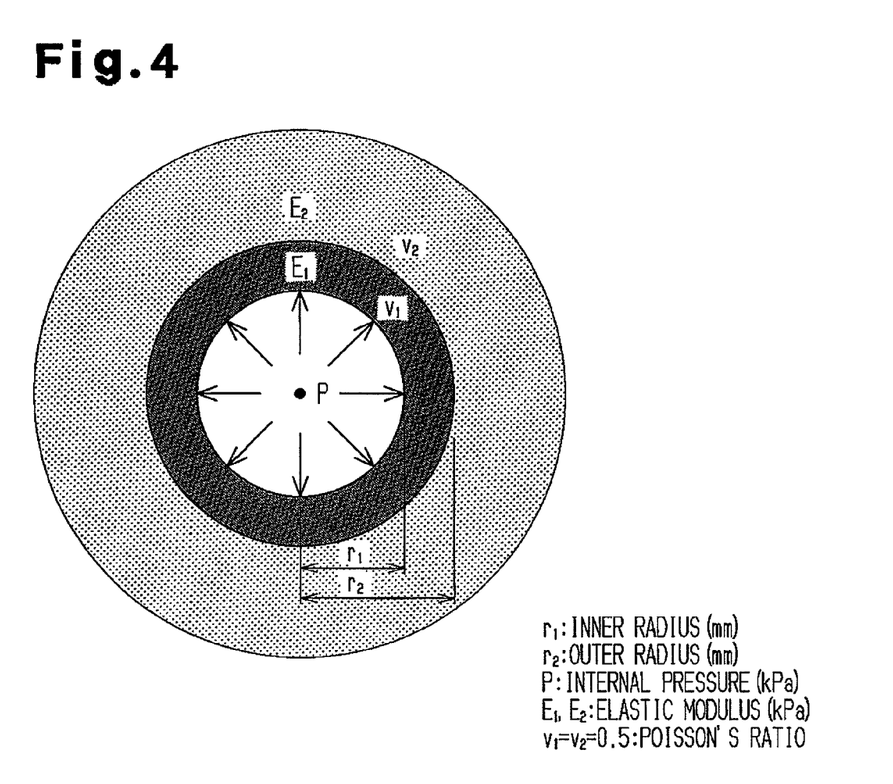
FIG. 4 is a conceptual diagram of a two-layer cylindrical model.

The carotid artery and the surrounding tissues can be modeled with a uniform two-layer cylinder (also referred to as "two-layer thick cylinder" in terms of strength of materials) as shown in FIG. 4. An inner radius of the carotid artery wall is designated by $r_1$, and an outer radius is designated by $r_2$. It is assumed that the surrounding tissues exist from the position apart from the center of the carotid artery by the length of $r_2$ to the infinity. Elastic modulus of the carotid artery wall is designated by $E_1$, and elastic modulus of the surrounding tissues is designated by $E_2$. A Poisson's ratio $v_1$ of the carotid artery wall and a Poisson's ratio $v_2$ of the surrounding tissues are both assumed to be 0.5. The amount of displacement h(r) of carotid artery and surrounding tissues with respect to a radial direction of the carotid artery when there is a change in the internal pressure (blood pressure) of the carotid artery from a specific reference state, in which the inner radius of the carotid artery wall is expressed by $r_1$ and the outer radius is expressed by $r_2$, can be expressed by the following Theoretical Equation (3) of a two-layer cylindrical model. In Equation (3), reference character P denotes the amount of change in the internal pressure from the reference state.

$$h(r) = \begin{cases} \dfrac{3(r^2(-E_2 + E_1) + r_2^2(E_2 + 3E_1))r_1^2 P}{2E_1 r(r_2^2(E_2 + 3E_1) + r_1^2(3E_2 - E_1))}, & r_1 \leq r \leq r_2 \\ \dfrac{6r_1^2 r_2^2 P}{r(r_2^2(E_2 + 3E_1) + r_1^2(3E_2 - E_1))}, & r \geq r_2 \end{cases} \quad (3)$$

The tissues at the distance of r from the center of the carotid artery move to the position of the distance of r+h(r) from the center of the carotid artery in accordance with the change in the internal pressure. The amount of displacement h is positive, thus, indicating expansion, when the amount of change P of the internal pressure is positive. The amount of displacement h is negative, thus, indicating contraction, when the amount of change P of the internal pressure is negative.

(Relationship between Elastic Modulus and Amount of Displacement of Carotid Artery and Surrounding Tissues)

The relationship between the elastic moduli $E_1$ and $E_2$ and the amount of displacement h(r) of a carotid artery and surrounding tissues will be described next.

Figure 6:
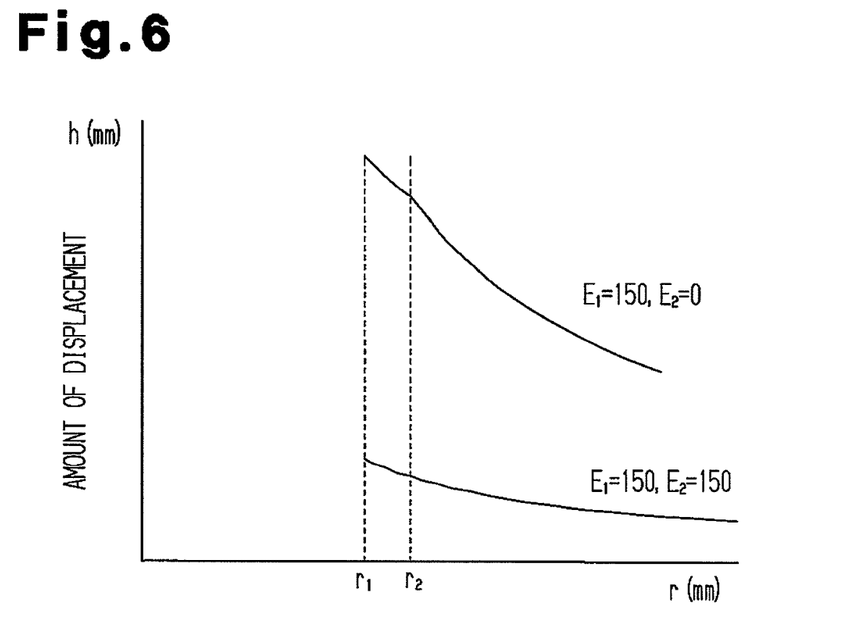
FIG. 6 is a graph showing the relationship between a distance r and an amount of displacement h in two two-layer cylindrical models, in which the elastic modulus $E_1$ of the carotid artery wall is the same, and the elastic modulus $E_2$ of the surrounding tissues is different.

FIG. 6 shows the relationship between a distance r from the center of a carotid artery and an amount of displacement h in two two-layer cylindrical models, in which elastic modulus $E_1$ of the carotid artery wall is the same, and elastic modulus $E_2$ of the surrounding tissues is different. The internal pressure of the carotid artery at a reference state is the same in the two-layer cylindrical models. As shown in FIG. 6, in both models, the amount of displacement h is maximum at a position where the distance r from the center of the carotid artery is equal to an inner radius $r_1$ of the carotid artery wall, thus, at the carotid artery wall inner surface, and becomes smaller as the distance r exceeds $r_1$ and becomes greater.

The variation in a carotid artery associated with heartbeats (heart rate variability of a carotid artery) can be considered as a time change in the amount of displacement h of the tissues at a position where the distance r from the center of the carotid artery is equal to $r_1$, thus, a time change in the amount of displacement $h(r_1)$. The fact that the heart rate variability of a carotid artery is affected by the elastic modulus $E_2$ of surrounding tissues is clear from the result of FIG. 6 showing that the amounts of displacement h(r) when the elastic modulus $E_2$ of the surrounding tissues is 150 kPa and when the elastic modulus $E_2$ is 0 kPa are different. Therefore, to more accurately estimate the elastic modulus $E_1$ of a carotid artery wall (blood vessel wall), the elastic modulus $E_2$ of surrounding tissues also needs to be estimated.

(Process of Image Processing Program)

Subsequently, a process of the image processing program executed by the CPU 41 of the image processing apparatus 11 will be described with reference to the flowchart of FIG. 5.

In advance, through input from the keyboard 15, the operator reads out moving images stored in the storage device 44 to display the moving images on a screen of the display 13 and designates a center of a carotid artery and an axis extending in the radial direction of the carotid artery on the displayed moving images. The CPU 41 sets the designated center and radial axis as an origin of reference coordinates and a reference axis, respectively.

Subsequently, the operator instructs the CPU 41 to start the process of the image processing program through the keyboard 15.

In response to the instruction, the CPU 41 calculates an amount of displacement of the carotid artery and the surrounding tissues with respect to the radial direction of the carotid artery at points on the designated radial axis according to an optical-flow technique in step S10. An arrow shown in FIG. 7(a) indicates the designated radial axis.

(Optical-Flow Technique)

The optical-flow technique will now be described.

The luminance of a point (x, y) on an image at a time t will be indicated by f(x, y, t). When a target moves by (Δx, Δy) after a very short time Δt, the following Equation (4) is established.

$$f(x,y,t)=f(x+\Delta x, y+\Delta y, t+\Delta t) \quad (4)$$

If the right hand member of Equation (4) is approximated by Taylor series up to the first order on the assumption that the amount of deviation (Δx, Δy) is small and locally constant, the following Equation (5) can be obtained.

$$f(x, y, t) = f(x, y, t) + \Delta x \frac{\partial f}{\partial x} + \Delta y \frac{\partial f}{\partial y} + \Delta t \frac{\partial f}{\partial t} \quad (5)$$

When ∂f/∂x, ∂f/∂y, and ∂f/∂t in Equation (5) are indicated by $f_x$, $f_y$, and $f_t$, respectively, and both members of Equation (5) are divided by Δt, the following Equation (6) can be obtained.

$$f_x \frac{\Delta x}{\Delta t} + f_y \frac{\Delta y}{\Delta t} + f_t = 0 \quad (6)$$

In Equation (6), Δx/Δt and Δy/Δt denote velocity of behavior in the x direction and velocity of behavior in the y direction, respectively, thus, velocity vectors. If Δx/Δt and Δy/Δt are indicated by u and v, respectively, Equation (6) can be rewritten by the following Equation (7).

$$f_x u + f_y v + f_t = 0 \quad (7)$$

Measuring $f_x$, $f_y$, and $f_t$ to solve Equation (7) can obtain a velocity field (u, v). However, Equation (7) cannot be solved because two unknown numbers are included. Therefore, an area D near a focused point is set for the focused point, and the velocity field is assumed to be constant in the area D to increase the number of equations. In this case, since there is no solution satisfying all equations, the velocity field is estimated so as to minimize a square integral J of the difference between the right hand member and the left hand member of Equation (7), which square integral J is shown in the following Equation (8).

$$J = \iint_D \{f_x u + f_y v + f_t\}^2 dx dy \quad (8)$$

If the square integral J is differentiated in relation to u and v and set to zero, the following Normal Equation (9) can be obtained.

$$uS_{xx} + vS_{xy} + S_{xt} = 0$$

$$uS_{xy} + vS_{yy} + S_{yt} = 0 \quad (9)$$

In Normal Equation (9), each S with a suffix denotes an integral value of a product of a derivative calculated in the following Equation (10).

$$S_{i,j} \stackrel{d}{=} \iint_D f_i f_j dx dy \quad (10)$$

i, j=x, y or t derivative

When values calculated by Equation (10) are assigned to Equation (9) to solve Equation (9), optical flows expressed by the following Equation (11), thus, velocity vectors (u, v), are obtained (thus, estimated). The method is called a local least squares method.

$$u = \frac{S_{yt}S_{xy} - S_{xt}S_{yy}}{S_{xx}S_{yy} - S_{xy}^2}, \; v = \frac{S_{xt}S_{xy} - S_{yt}S_{xx}}{S_{xx}S_{yy} - S_{xy}^2} \quad (11)$$

In the present embodiment, the velocity vector (u, v) at each designated point (each pixel) on the designated axis extending in the radial direction of the carotid artery is obtained. Subsequently, the amount of displacement is obtained by multiplying the velocity vector (u, v) at each point by the time difference between frames of images used to obtain the velocity vector. More specifically, among the images video captured at several dozen frames/second, an image of a frame at blood pressure diastolic, thus, at the largest contraction of carotid artery, and an image of a frame at blood pressure systolic, thus, at the largest expansion of carotid artery, are extracted to estimate the optical flow of each point on the designated radial axis from the images of two frames. Based on the estimated optical flow of each point, the amount of displacement of the carotid artery and the surrounding tissues with respect to the radial direction of the carotid artery is calculated at each point on the designated radial axis.

In step S20 following step S10, the CPU 41 calculates the elastic modulus $E_1$ of a carotid artery wall, the elastic modulus $E_2$ of surrounding tissues, and the inner radius $r_1$ and the outer radius $r_2$ of a carotid artery to minimize the square error between the amount of displacement of the carotid artery and the surrounding tissues with respect to the radial direction of the carotid artery at the points on the designated radial axis and the amount of displacement h of the carotid artery and the surrounding tissues with respect to the radial direction of the carotid artery calculated based on Theoretical Equation (3) provided by the two-layer cylindrical model. In that case, the difference between the blood pressure systolic and the blood pressure diastolic measured from the subject using a blood pressure measurement apparatus (not shown) is assigned to the amount of change P of the internal pressure in Theoretical Equation (3).

In the following step S30, the CPU 41 outputs the elastic modulus $E_1$ of the carotid artery wall, the elastic modulus $E_2$ of the surrounding tissues, and the inner radius $r_1$ and the outer radius $r_2$ of the carotid artery calculated in step S20 to the display 13 and the printer 14. The CPU 41 then ends the image processing program.

According to the present embodiment, the following advantages are obtained.

(1) In the image processing apparatus 11 of the present embodiment, the computer 12 functions as first calculation means for acquiring a moving image including a minor axis cross section of a carotid artery and a cross section of surrounding tissues around the carotid artery, estimating, from images of two temporally different frames of the acquired moving image, an optical flow of each point included in an area corresponding to a carotid artery wall and an optical flow of each point included in an area corresponding to the surrounding tissues, and calculating, based on the estimated optical flow of each point, an amount of displacement of the carotid artery and the surrounding tissues with respect to a radial direction of the carotid artery depending on a change in internal pressure of the carotid artery. The computer 12 also functions as second calculation means for calculating an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder and estimating elastic modulus of the carotid artery wall and the elastic modulus of the surrounding tissues so as to minimize a square error between the two calculated amounts of displacement. As a result, since the surrounding tissues of the carotid artery are taken into consideration, the elastic modulus of the carotid artery wall can be calculated more accurately.

(2) The image processing apparatus 11 of the present embodiment estimates the optical flow of each point (each pixel) on an axis extending in the radial direction of the carotid artery from the images of the two temporally different frames and calculates, based on the estimated optical flow of each point, the amount of displacement of the carotid artery and the surrounding tissues with respect to the radial direction of the carotid artery depending on a change in the internal pressure of the carotid artery. In this case, the time required to estimate the optical flows is reduced compared to when the optical flows of all pixels included in the area corresponding to the carotid artery wall and the area corresponding to the surrounding tissues are estimated.

(3) The image processing program of the present embodiment causes the computer 12 to function to acquire a moving image including a minor axis cross section of a carotid artery and a cross section of surrounding tissues around the carotid artery, estimate, from images of two temporally different frames of the acquired moving image, an optical flow of each point included in an area corresponding to a carotid artery wall and an optical flow of each point included in an area corresponding to the surrounding tissues, and calculate, based on the estimated optical flow of each point, an amount of displacement of the carotid artery and the surrounding tissues related to a radial direction of the carotid artery depending on a change in internal pressure of the carotid artery. The image processing program also causes the computer 12 to function to calculate an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder and estimate the elastic modulus of the carotid artery wall and the elastic modulus of the surrounding tissues so as to minimize a margin of error between the calculated two amounts of displacement. As a result, since the surrounding tissues of the carotid artery are taken into consideration, a computer can function as an image processing apparatus that can more accurately calculate the elastic modulus of the carotid artery wall.

(4) The image processing program of the present embodiment causes the computer 12 to function to estimate the optical flow of each point (each pixel) on an axis extending in the radial direction of the carotid artery from the images of the two temporally different frames and calculate, based on the estimated optical flow of each point, the amount of displacement of the carotid artery and the surrounding tissues with respect to the radial direction of the carotid artery depending on a change in the internal pressure of the carotid artery. In this case, the time required to estimate the optical flows is reduced compared to when the optical flows of all pixels included in the area corresponding to the carotid artery wall and the area corresponding to the surrounding tissues are estimated.

(5) The ROM 42 of the present embodiment functions as a storage medium storing the image processing program. Since the CPU 41 of the computer 12 executes the image processing program, the surrounding tissues of the carotid artery are taken into consideration. Therefore, the elastic modulus of the carotid artery wall can be more accurately calculated.

(6) Since the ultrasonic diagnostic equipment 16 of the present embodiment is connected to the image processing apparatus 11, the advantages of (1) and (2) are easily achieved.

EXAMPLE

The ultrasonic diagnostic equipment used in an example was SonoAce PICO manufactured by Medison Japan, Inc. A linear-type ultrasound probe (7.5M Hz) was applied to a carotid artery part of a subject to capture moving images of B-mode minor axis cross sections of the carotid artery. The captured B-mode images were outputted from the video output of the ultrasonic diagnostic equipment, video captured by a DV converter (ADVC-300 manufactured by CANOPUS) at resolution 720×480 pixels and 30 frames/second, and then imported to the computer 12 as an IEEE1394 signal. The number of pixels of the ultrasound image area displayed by the display 13 was 540 pixels in the horizontal direction and 420 pixels in the vertical direction. The pixel size was 0.0713 mm/pixel.

Figure 7A:
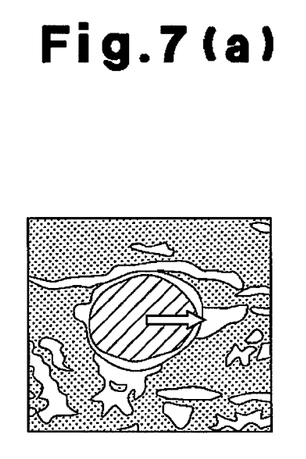
Figure 7B:
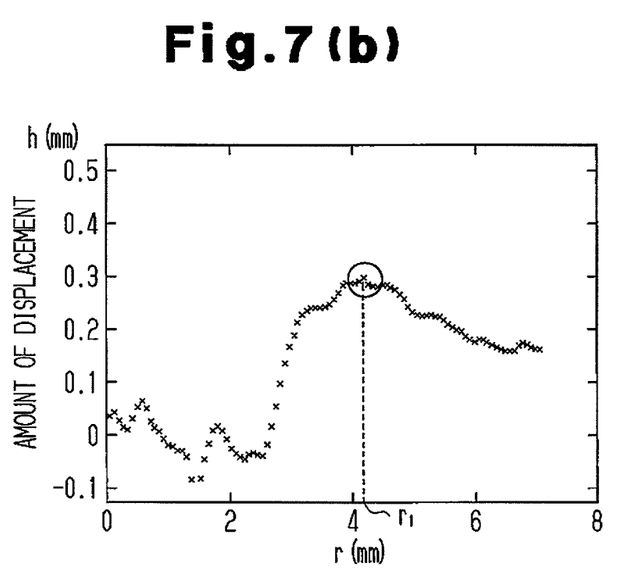

A frame at blood pressure diastolic and a frame at blood pressure systolic were extracted from the acquired moving images, and an amount of displacement of the carotid artery and the surrounding tissues with respect to the radial direction of the carotid artery were calculated from the images of both frames in accordance with the optical-flow technique. FIG. 7(b) shows the result of the calculation of the amount of displacement of the carotid artery and the surrounding tissues with respect to the radial direction of the carotid artery at each point on an axis extending in the radial direction of the carotid artery shown by the arrow in FIG. 7(a).

Values of the elastic modulus $E_1$ of the carotid artery wall, the elastic modulus $E_2$ of the surrounding tissues, and the inner radius $r_1$ and the outer radius $r_2$ of the carotid artery were calculated to minimize a square error between the amount of displacement h(r) estimated as described above and the amount of displacement h(r) of the carotid artery and the surrounding tissues with respect to the radial direction of the carotid artery calculated based on Theoretical Equation (3) provided by the two-layer cylindrical model. As a result, the calculated values indicated 70 kPa in relation to the elastic modulus $E_1$ of the carotid artery wall, 141 kPa in relation to the elastic modulus $E_2$ of the surrounding tissues, 4.2 mm in relation to the inner radius $r_1$ of the carotid artery, and 5.1 mm in relation to the outer radius $r_2$ of the carotid artery. The amount of displacement h(r) least-squares-estimated at this point is illustrated by a curve of solid line in the graph of FIG. 8(a).

Meanwhile, when the value of the elastic modulus $E_1$ of the carotid artery wall was calculated in accordance with the same procedure as mentioned above except that the elastic modulus $E_2$ of the surrounding tissues was assumed to be 0 kPa, the value of the calculated elastic modulus $E_1$ was 420 kPa. The amount of displacement h(r) least-squares-estimated at this point is illustrated by a curve of solid line in the graph of FIG. 8(b). Such a method of calculating the elastic modulus $E_1$ of the carotid artery wall is equivalent to a conventional method in that the surrounding tissues of the carotid artery are not taken into consideration.

Figure 9A:
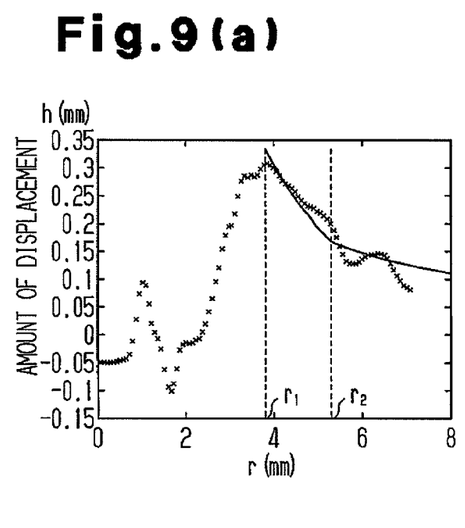
Figure 9B:
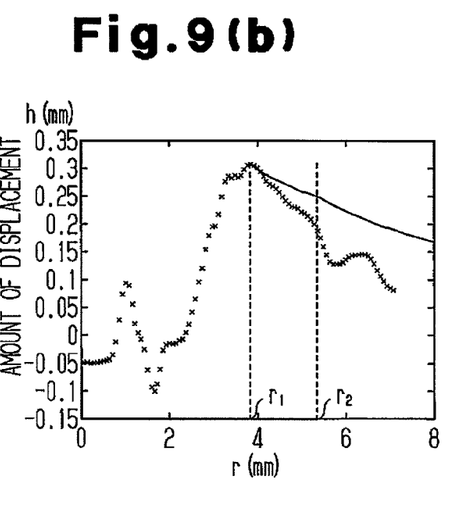
Figure 10A:
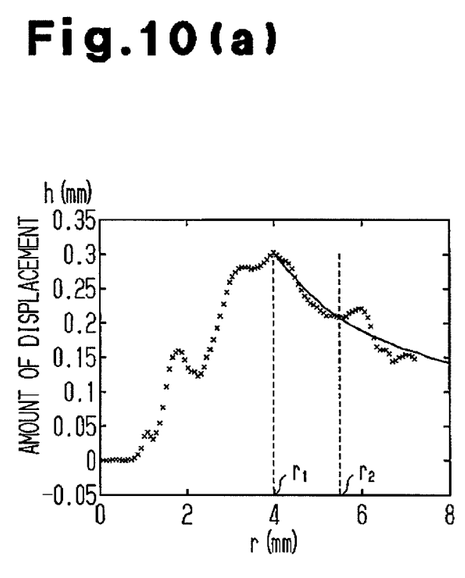
Figure 10B:
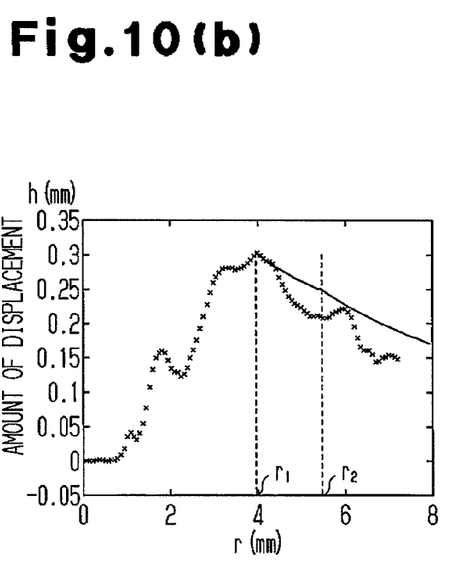

FIGS. 9(a) and 9(b) show the result of performing the same measurement for another subject, and FIGS. 10(a) and 10(b) show the result of performing the same measurement for yet another subject.

In the measurements the results of which are shown in FIGS. 9(a) and 9(b), when the values of the elastic modulus $E_1$ of the carotid artery wall, the elastic modulus $E_2$ of the surrounding tissues, and the inner radius $r_1$ and the outer radius $r_2$ of the carotid artery were calculated according to the method of the present invention, the calculated values indicated 40 kPa, 186 kPa, 3.8 mm, and 5.3 mm, respectively. Meanwhile, when the value of the elastic modulus $E_1$ of the carotid artery wall was calculated in accordance with a conventional method, the value of the calculated elastic modulus $E_1$ was 238 kPa. In the graphs of FIGS. 9(a) and 9(b), a plot indicated by "x" denotes the amount of displacement h(r) calculated according to the optical-flow technique. Meanwhile, the curve shown by a solid line in the graph of FIG. 9(a) denotes the amount of displacement h(r) least-squares-estimated according to the method of the present invention, and the curve shown by a solid line in the graph of FIG. 9(b) denotes the amount of displacement h(r) least-squares-estimated according to the conventional method.

In the measurements the results of which are shown in FIGS. 10(a) and 10(b), when the values of the elastic modulus $E_1$ of the carotid artery wall, the elastic modulus $E_2$ of the surrounding tissues, and the inner radius $r_1$ and the outer radius $r_2$ of the carotid artery were calculated according to the method of the present invention, the calculated values are 81 k Pa, 129 kPa, 3.95 mm, and 5.46 mm, respectively. Meanwhile, when the value of the elastic modulus $E_1$ of the carotid artery wall was calculated in accordance with a conventional method, the value of the calculated elastic modulus $E_1$ was 260 kPa. In the graphs of FIGS. 10(a) and 10(b), a plot indicated by "x" denotes the amount of displacement h(r) calculated according to the optical-flow technique. Meanwhile, the curve shown by a solid line in the graph of FIG. 10(a) denotes the amount of displacement h(r) least-squares-estimated according to the method of the present invention, and the curve shown by a solid line in the graph of FIG. 10(b) denotes the amount of displacement h(r) least-squares-estimated according to the conventional method.

Figure 8A:
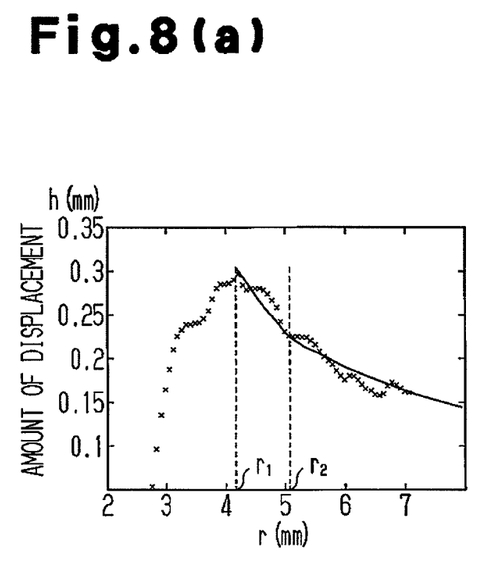
Figure 8B:
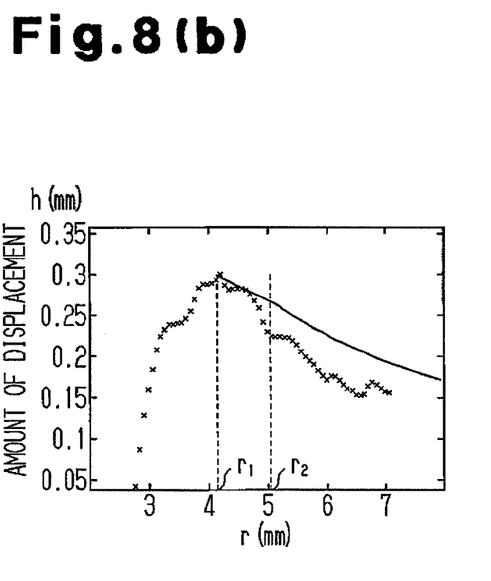

In all of the measurements the results of which are shown in FIGS. 8(a) and 8(b), the measurements the results of which are shown in FIGS. 9(a) and 9(b), and the measurements the results of which are shown in FIGS. 10(a) and 10(b), the value of the elastic modulus $E_1$ of the carotid artery wall calculated according to the conventional method is greater than the value of the elastic modulus $E_1$ of the carotid artery wall calculated according to the method of the present invention. This indicates that there is a possibility in the conventional method that the arteriosclerosis may be assumed to have progressed further than it actually is.

The embodiment may be changed and configured as follows.

Figure 5:
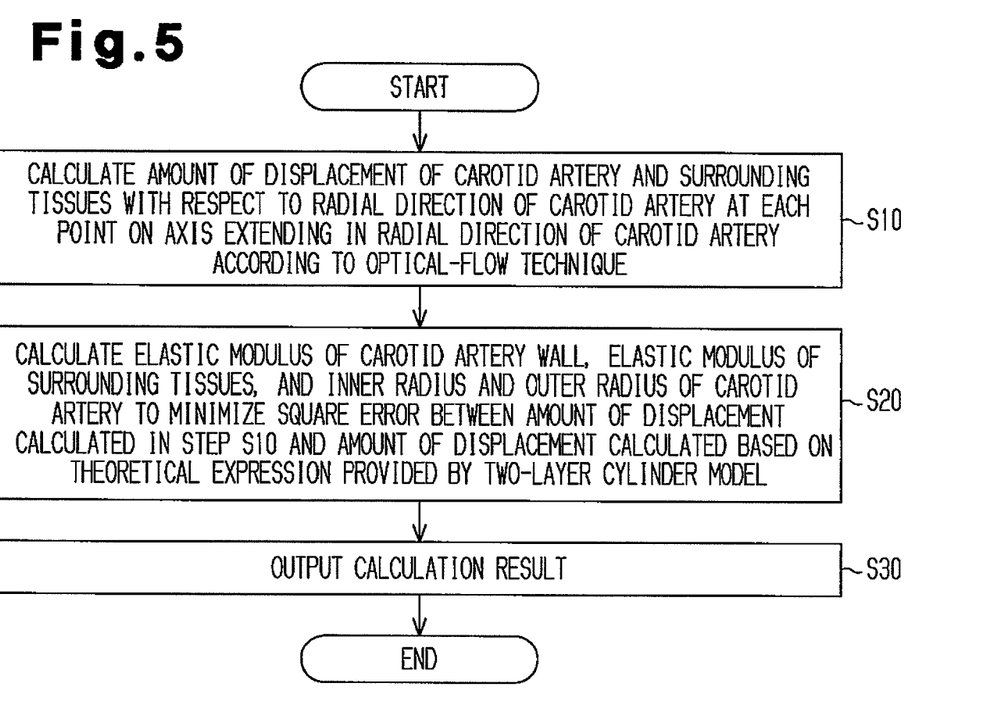
FIG. 5 is a flowchart of an image processing program executed by a computer.

In step S20 of the flowchart of FIG. 5, the elastic modulus $E_1$ of the carotid artery wall, the elastic modulus $E_2$ of the surrounding tissues, and the inner radius $r_1$ and the outer radius $r_2$ of the carotid artery are calculated to minimize the square error between the amount of displacement calculated according to the optical-flow technique and the amount of displacement calculated based on theoretical equation provided by the two-layer cylindrical model in the present embodiment. However, since the amount of displacement is maximum at the position where the distance r from the center of the carotid artery is equal to the inner radius $r_1$ of the carotid artery wall (see FIG. 7(b)), the distance r where the amount of displacement calculated according to the optical-flow technique is maximum may be determined in advance as the inner radius $r_1$ of the carotid artery wall.

Instead of estimating the optical flow of each point (each pixel) on the axis extending in the radial direction of the carotid artery, optical flows of all pixels included in the area corresponding to the carotid artery wall and the area corresponding to the surrounding tissues on the ultrasound B-mode images may be estimated.

In place of the ROM 42, the storage device 44 may be used as the storage medium for storing the image processing program. Alternatively, the image processing program may be stored in a storage medium, such as a CD, a DVD, and a USB memory, and a driver device may be used to load the image processing program stored in the storage medium from the storage device to execute the program.

While the invention has been described in detail and with reference to specific embodiments thereof, it will be apparent to one skilled in the art that various changes and modifications can be made therein without departing from the spirit and scope thereof.

The invention claimed is:

1. An image processing apparatus comprising:
a first calculation unit for acquiring a moving image including a minor axis cross section of a carotid artery and a cross section of surrounding tissues around the carotid artery, estimating, from images of two temporally different frames of the acquired moving image, an optical flow of each point included in an area corresponding to a carotid artery wall and an optical flow of each point included in an area corresponding to the surrounding tissues, and calculating, based on the estimated optical flow of each point, an amount of displacement of the carotid artery and the surrounding tissues with respect to a radial direction of the carotid artery depending on a change in internal pressure of the carotid artery; and
a second calculation unit for calculating an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder and calculating the elastic modulus of the carotid artery wall and the elastic modulus of the surrounding tissues so as to minimize a square error between the thus calculated amount of displacement and the amount of displacement calculated by the first calculation unit.

2. The image processing apparatus according to claim 1, wherein the first calculation unit estimates the optical flow of each point on an axis extending in the radial direction of the carotid artery from the images of the two frames and calculates, based on the estimated optical flow of each point, the amount of displacement of the carotid artery and the surrounding tissues with respect to the radial direction of the carotid artery depending on a change in the internal pressure of the carotid artery.

3. A non-transitory computer readable medium having stored thereon a computer executable image processing program which, when executed, causes a computer to implement:
a first calculation unit for acquiring a moving image including a minor axis cross section of a carotid artery and a cross section of surrounding tissues around the carotid artery, estimating, from images of two temporally different frames of the acquired moving image, an optical flow of each point included in an area corresponding to a carotid artery wall and an optical flow of each point included in an area corresponding to the surrounding tissues, and calculating, based on the estimated optical flow of each point, an amount of displacement of the carotid artery and the surrounding tissues with respect to a radial direction of the carotid artery depending on a change in internal pressure of the carotid artery; and a second calculation unit for calculating an amount of displacement of the carotid artery and the surrounding tissues with respect to the radial direction of the carotid artery depending on a change in the internal pressure of the carotid artery based on a theoretical expression obtained by modeling the carotid artery and the surrounding tissues with a two-layer cylinder and calculating the elastic modulus of the carotid artery wall and the elastic modulus of the surrounding tissues so as to minimize a square error between the thus calculated amount of displacement and the amount of displacement calculated by the first calculation unit.

4. The non-transitory computer readable medium according to claim 3, wherein the first calculation unit estimates the optical flow of each point on an axis extending in the radial direction of the carotid artery from the images of the two frames and calculates, based on the estimated optical flow of each point, the amount of displacement of the carotid artery and the surrounding tissues with respect to the radial direction of the carotid artery depending on a change in the internal pressure of the carotid artery.

5. Ultrasonic diagnostic equipment being connected to the image processing apparatus according to claim 1, generating an ultrasound B-mode image based on an echo signal obtained through transmission and reception of ultrasound by a probe, and outputting the generated ultrasound B-mode image to the image processing apparatus.

\* \* \* \* \*